United States Patent
Reddy et al.

(10) Patent No.: US 9,932,307 B2
(45) Date of Patent: Apr. 3, 2018

(54) PROCESS FOR ANNEALING AMORPHOUS ATORVASTATIN

(71) Applicant: Pfizer Inc., New York, NY (US)

(72) Inventors: Renuka Devi Reddy, Waterford, CT (US); Evgenyi Shalaev, Dana Point, CA (US); Ravi Mysore Shanker, Stonington, CT (US); Carl Bernard Ziegler, East Lyme, CT (US)

(73) Assignee: Pfizer Inc., New York, NY (US)

( * ) Notice: Subject to any disclaimer, the term of this patent is extended or adjusted under 35 U.S.C. 154(b) by 61 days.

(21) Appl. No.: 15/220,897

(22) Filed: Jul. 27, 2016

(65) Prior Publication Data

US 2016/0332965 A1    Nov. 17, 2016

Related U.S. Application Data

(60) Continuation of application No. 14/688,451, filed on Apr. 16, 2015, now Pat. No. 9,428,455, which is a division of application No. 12/067,056, filed as application No. PCT/IB2006/002648 on Sep. 11, 2006, now Pat. No. 9,034,913.

(60) Provisional application No. 60/758,270, filed on Jan. 10, 2006, provisional application No. 60/719,258, filed on Sep. 21, 2005.

(51) Int. Cl.
*C07D 207/34* (2006.01)
*A61K 31/40* (2006.01)

(52) U.S. Cl.
CPC ............ *C07D 207/34* (2013.01); *A61K 31/40* (2013.01)

(58) Field of Classification Search
CPC .............................. C07D 207/34; A61K 31/40
See application file for complete search history.

(56) References Cited

U.S. PATENT DOCUMENTS

| | | |
|---|---|---|
| 4,681,893 A | 6/1987 | Roth |
| 5,003,080 A | 3/1991 | Butler et al. |
| 5,097,045 A | 3/1992 | Butler et al. |
| 5,103,024 A | 4/1992 | Millar et al. |
| 5,124,482 A | 6/1992 | Butler et al. |
| 5,149,837 A | 9/1992 | Butler et al. |
| 5,155,251 A | 10/1992 | Butler et al. |
| 5,216,174 A | 6/1993 | Butler et al. |
| 5,245,047 A | 9/1993 | Butler et al. |
| 5,248,793 A | 9/1993 | Millar et al. |
| 5,273,995 A | 12/1993 | Roth |
| 5,280,126 A | 1/1994 | Butler et al. |
| 5,298,627 A | 3/1994 | Butler et al. |
| 5,342,952 A | 8/1994 | Butler et al. |
| 5,397,792 A | 3/1995 | Butler et al. |

(Continued)

FOREIGN PATENT DOCUMENTS

| | | |
|---|---|---|
| WO | 0136384 | 5/2001 |
| WO | 02057228 | 7/2002 |

(Continued)

OTHER PUBLICATIONS

Berge, S. M., et al., Pharmaceutical Sals, Journal of Pharmaceutical Sciences, 86(1), pp. 1-19, (1977).

(Continued)

*Primary Examiner* — Trevor Love
(74) *Attorney, Agent, or Firm* — Stephanie J. Monaco

(57) ABSTRACT

Processes for annealing amorphous atorvastatin is described. Pharmaceutical compositions and formulations containing annealed amorphous atorvastatin are also described.

11 Claims, 9 Drawing Sheets

(56) References Cited

U.S. PATENT DOCUMENTS

| | | |
|---|---|---|
| 5,446,054 A | 8/1995 | Butler et al. |
| 5,470,981 A | 11/1995 | Butler et al. |
| 5,489,690 A | 2/1996 | Butler et al. |
| 5,489,691 A | 2/1996 | Butler et al. |
| 5,510,488 A | 4/1996 | Butler et al. |
| 5,686,104 A | 11/1997 | Mills et al. |
| 5,969,156 A | 10/1999 | Briggs et al. |
| 5,998,633 A | 12/1999 | Jacks et al. |
| 6,087,511 A | 7/2000 | Lin et al. |
| 6,106,864 A | 8/2000 | Dolan et al. |
| 6,121,461 A | 9/2000 | McKenzie |
| 6,126,971 A | 10/2000 | Mills et al. |
| 6,433,213 B1 | 8/2002 | Bosch et al. |
| 6,476,235 B2 | 11/2002 | Butler et al. |
| 6,528,660 B1 | 3/2003 | Kumar et al. |
| 6,528,661 B2 | 3/2003 | Niddam et al. |
| 6,598,010 B2 | 7/2003 | Zefira |
| 6,605,636 B2 | 8/2003 | Aronhime et al. |
| 6,605,759 B1 | 8/2003 | Hicks |
| 6,613,916 B2 | 9/2003 | Pflaum |
| 6,646,133 B1 | 11/2003 | Greff et al. |
| 6,867,306 B2 | 3/2005 | Srinath et al. |
| 6,891,047 B2 | 5/2005 | Pflaum |
| 7,030,151 B2 | 4/2006 | Kerc et al. |
| 7,074,818 B2 | 7/2006 | Manne et al. |
| 7,074,940 B2 | 7/2006 | Sorsak |
| 7,230,120 B2 | 6/2007 | Poornaprajna et al. |
| 7,256,212 B2 | 8/2007 | Tessler et al. |
| 2003/0114357 A1 | 6/2003 | Fryburg et al. |
| 2003/0114686 A1 | 6/2003 | Van Der Schaaf et al. |
| 2004/0077708 A1 | 4/2004 | Grahek et al. |
| 2004/0185102 A1 | 9/2004 | Friesen et al. |
| 2004/0253305 A1 | 12/2004 | Luner et al. |
| 2005/0032880 A1 | 2/2005 | Lorenz et al. |
| 2005/0209306 A1 | 9/2005 | Jegorov et al. |
| 2006/0122403 A1 | 6/2006 | Suri et al. |
| 2007/0225353 A1 | 9/2007 | Leonard et al. |

FOREIGN PATENT DOCUMENTS

| | | |
|---|---|---|
| WO | 02083637 | 10/2002 |
| WO | 02083638 | 10/2002 |
| WO | 2004043918 | 5/2004 |
| WO | 2005011638 | 2/2005 |

OTHER PUBLICATIONS

Konno, T., Physical and Chemical Changes of Medicinals in Mixtures with Adsorbents in the Solid State. IV. Study on Reduced-Pressure Mixing for Practical Use of Amorphous Mixtures of Flufenamic Acid, Chem. Pharm. Bull., 38(7), pp. 2003-2007, (1990).

Liang, A. C., et al., Fast-dissolving intraoral drug delivery systems, Expert Opinion Ther. Patents, 11(6), pp. 981-986, (2001).

Takemoto, M., et al., Statins as antioxidant therapy for preventing cardiac myocite hypertrophy, J. Clin. Invest., 108:1429-1437,(2001).

U.S. Appl. No. 60/623,086, filed Oct. 28, 2004.

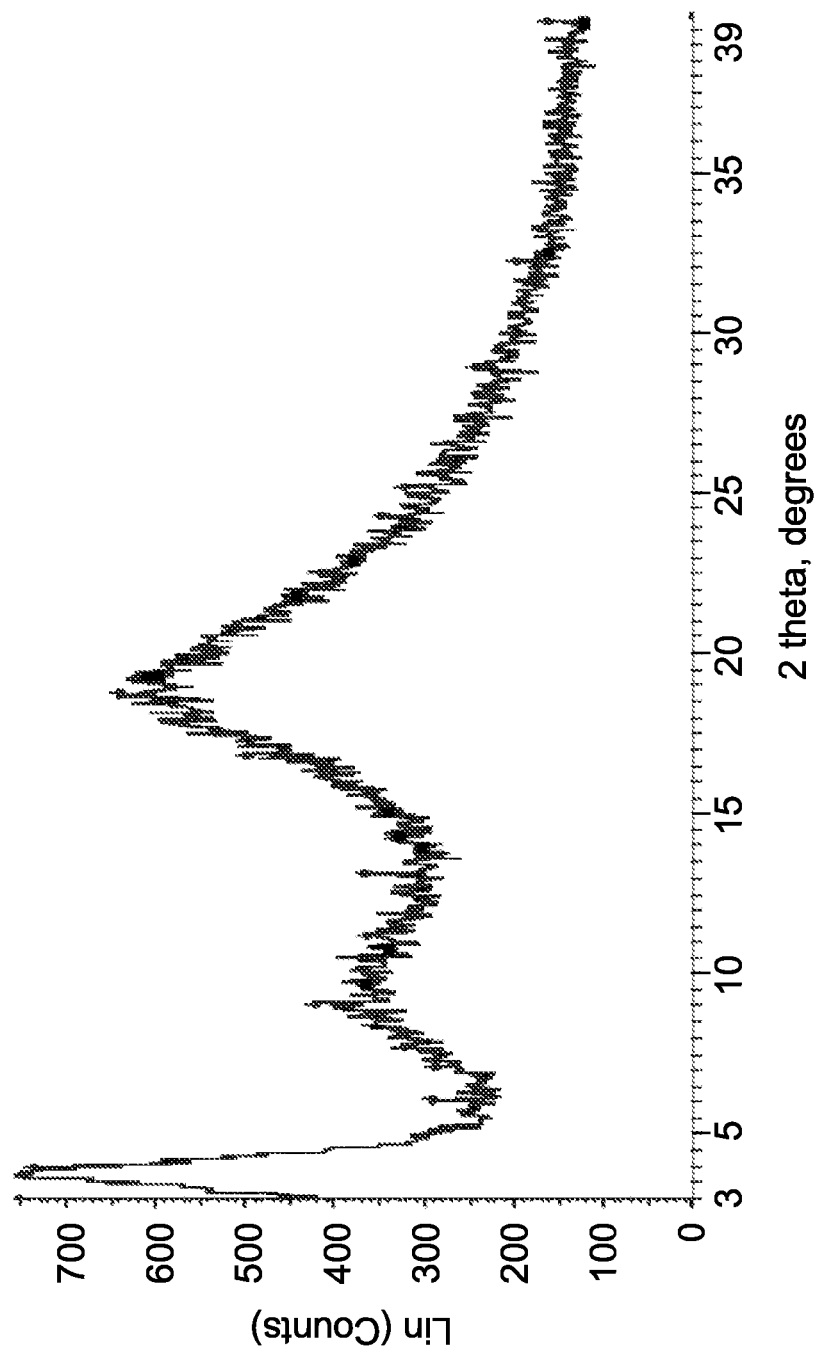

PROCESS FOR ANNEALING AMORPHOUS ATORVASTATIN

This application is a continuation application of U.S. Ser. No. 14/688,451 filed Apr. 16, 2015, now pending which is a divisional application of U.S. Ser. No. 12/067,056 filed Aug. 19, 2008, now U.S. Pat. No. 9,034,913, which is a 371 application of PCT/IB2006/002648 filed on Sep. 11, 2006, which claims the benefit of provisional application U.S. Ser. No. 60/758,270 filed on Jan. 10, 2006 and provisional application U.S. Ser. No. 60/719,258 filed on Sep. 21, 2005, all of which are incorporated herein by reference in their entirety

FIELD OF THE INVENTION

The invention relates to processes for annealing amorphous atorvastatin as well as compositions and pharmaceutical formulations containing annealed amorphous atorvastatin. The annealed amorphous atorvastatin is more stable than amorphous atorvastatin that has not been annealed.

BACKGROUND OF THE INVENTION

The conversion of 3-hydroxy-3-methylglutaryl-coenzyme A (HMG-CoA) to mevalonate is an early and rate-limiting step in the cholesterol biosynthetic pathway. This step is catalyzed by the enzyme HMG-CoA reductase. Statins inhibit HMG-CoA reductase from catalyzing this conversion. As such, statins are collectively potent lipid lowering agents.

Atorvastatin and pharmaceutically acceptable salts thereof are selective, competitive inhibitors of HMG-CoA reductase. Atorvastatin calcium is currently sold as LIPITOR® having the chemical name [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1) trihydrate and the formula

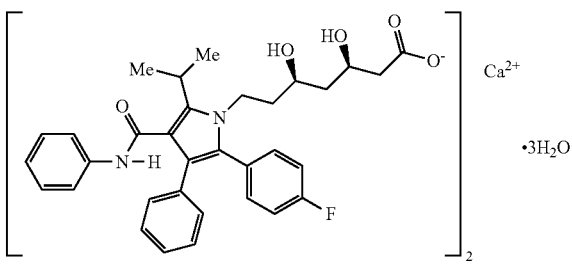

As such, atorvastatin calcium is a potent lipid-lowering compound and is thus useful as a hypolipidemic and/or hypocholesterolemic agent. Atorvastatin calcium is also useful in the treatment of osteoporosis, benign prostatic hyperplasia (BPH) and Alzheimer's disease.

A number of patents and published International Patent Applications have issued describing atorvastatin, formulations of atorvastatin, as well as processes and key intermediates for preparing atorvastatin. These include: U.S. Pat. Nos. 4,681,893; 5,273,995; 5,003,080; 5,097,045; 5,103,024; 5,124,482; 5,149,837; 5,155,251; 5,216,174; 5,245,047; 5,248,793; 5,280,126; 5,397,792; 5,342,952; 5,298,627; 5,446,054; 5,470,981; 5,489,690; 5,489,691; 5,510,488; 5,686,104; 5,969,156; 5,998,633; 6,087,511; 6,121,461; 6,126,971; 6,433,213; 6,476,235; 6,605,759; WO 01/36384; WO 02/41834; WO 02/43667; WO 02/43732; WO 02/051804; WO 02/057228; WO 02/057229; WO 02/057274; WO 02/059087; WO 02/083637; WO 02/083638; WO 03/011826; WO 03/050085; WO 03/07072; and WO 04/022053.

It has been described that the amorphous forms of a number of drugs exhibit different dissolution characteristics and in some cases different bioavailability patterns compared to the crystalline form (Konno T., *Chem. Pharm. Bull.*, 1990; 38:2003-2007). For some therapeutic indications, one bioavailability pattern may be favored over another.

Variations in dissolution rates can make it advantageous to produce atorvastatin formulations in either crystalline or amorphous forms. For example, for some potential uses of atorvastatin (e.g., acute treatment of patients having strokes as described in Takemoto, M.; Node, K.; Nakagami, H.; Liao, Y.; Grimm; M.; Takemoto, Y.; Kitakaze, M.; Liao, J. K., *Journal of Clinical Investigation*, 2001; 108(10): 1429-1437), a rapid onset of activity may be highly beneficial in improving the efficacy of atorvastatin.

The preparation of amorphous atorvastatin has been previously described. For example, Lin et al., U.S. Pat. No. 6,087,511, describe forming amorphous atorvastatin from crystalline atorvastatin. To form amorphous atorvastatin, Lin et al. describe that crystalline atorvastatin is dissolved in a non-hydroxylic solvent such as tetrahydrofuran. The non-hydroxylic solvent is removed to produce a brittle foam that is broken up by mechanical agitation to afford amorphous atorvastatin.

WO 00/71116 also describes forming amorphous atorvastatin using a non-hydroxylic solvent.

WO 01/28999 describes a process for forming amorphous atorvastatin calcium by recrystallization of crude atorvastatin from an organic solvent which comprises dissolving crude amorphous atorvastatin calcium in a lower alkanol containing 2-4 carbon atoms or a mixture of such alkanols under heating and isolating the amorphous atorvastatin calcium precipitated after cooling.

WO 01/42209 describes preparing amorphous atorvastatin by precipitating the atorvastatin using a solvent in which atorvastatin is insoluble or very slightly soluble, from a solution of atorvastatin which is provided with a solvent in which atorvastatin is freely soluble. Preferred solvents in which atorvastatin is freely soluble include low molecular weight alcohols, e.g. methanol and ethanol.

WO 03/078379 describes forming amorphous atorvastatin by dissolving atorvastatin in a hydroxylic solvent and removing the solvent by either freeze-drying or spray drying.

US Published Patent Application 2004/0024046 A1 describes a process for forming amorphous atorvastatin by precipitating atorvastatin from a solution with a solvent in which atorvastatin is insoluble or very slightly soluble.

The use of amorphous pharmaceutical substances, such as amorphous atorvastatin calcium, can be beneficial because such disordered materials usually have higher solubility and bioavailability. However, an unsatisfactory characteristic shared by amorphous drug substances is that they usually have lower physical and chemical stabilities, thus reducing their shelf life over crystalline drug substances. Thus, amorphous atorvastatin is susceptible to degradation upon storage. Once degraded, the drug material may not be acceptable for some medical uses. As a result, there is a need to develop methods for stabilizing amorphous atorvastatin.

SUMMARY OF THE INVENTION

These and other needs are met by the present invention which is directed to a method for annealing amorphous atorvastatin, either alone or as part of a pharmaceutical composition/formulation, each as described herein. By annealing amorphous atorvastatin according to the procedure developed by the inventors and described herein leads to surprisingly higher levels of improved stability compared to non-annealed amorphous atorvastatin samples; that is, annealed atorvastatin samples had a lower rate of chemical degradation compared to non-annealed samples. Thus, annealed amorphous atorvastatin can be stored for longer periods than non-annealed amorphous atorvastatin, and can be used to prepare pharmaceutical dosage forms with enhanced stability profiles as compared to dosage forms containing non-annealed amorphous atorvastatin.

Thus, the Invention is directed to a process for annealing amorphous atorvastatin at elevated temperature comprising heating at ambient pressure amorphous atorvastatin in an essentially solvent-free system to a temperature of between approximately 50° C. to approximately 140° C.; holding the temperature for approximately 1 minute to approximately 30 days to provide the annealed amorphous atorvastatin; and cooling the resulting annealed amorphous atorvastatin. In one embodiment, the time is as provided earlier and the temperature is between approximately 80° C. to approximately 110° C. In another embodiment, the time is as provided earlier and the temperature is between approximately 90° C. to approximately 105° C. In another embodiment, the temperature is as provided earlier and the time is between approximately 10 minutes and approximately 72 hours. In another embodiment, the temperature is as provided earlier and the time is between approximately 30 minutes and approximately 12 hours. In a preferred embodiment, the temperature is as provided earlier wherein the time is between approximately 1 and 6 hours.

The invention is also directed to a process for annealing amorphous atorvastatin at elevated or high pressure. According to the invention, such a process comprises treating amorphous atorvastatin at a pressure of between approximately 0.1 kBar to approximately 250 kBar at a temperature of between ambient temperature (approximately 20° C.) to approximately 150° C. for approximately 1 minute to approximately 30 days. In one embodiment, the temperature and time are as provided earlier and the pressure is between approximately 0.5 kBar and approximately 200 kBar. In one embodiment, the temperature and time are as provided earlier and the pressure is between approximately 0.5 kBar and approximately 10 kBar. In another embodiment, the pressure and time are as provided earlier and the temperature is between approximately 25° C. to approximately 80° C. In another embodiment, the pressure and temperature are as provided earlier and the time is between approximately 30 minutes and approximately 12 hours. In another embodiment, the temperature and time are as provided earlier and the pressure is cycled between about ambient pressure and about 200 kBars two or more times. As would be understood by one of ordinary skill in the art, elevated pressures may be achieved using techniques known in the art.

The invention is also directed to a process for annealing amorphous atorvastatin comprising irradiating amorphous atorvastatin with microwave at a frequency ranging from about 1 GHz to about 100 GHz and power of about 1 watt (W) to about 3000 watts (W) either in a continuous or pulse mode for a time period ranging from about 1 second to about 10 hours. In one embodiment, amorphous atorvastatin is irradiated with microwave frequency of about 2.45 GHz and power of about 10 W to about 500 W in a continuous mode range for a time period of about 10 seconds to about 10 hours. In another embodiment, amorphous atorvastatin is irradiated from about 1 minute up to about 10 hours with microwave at a frequency of about 2.45 GHz and power of about 1 W to about 3000 W in a pulse mode range for a pulse time period of about 10 to about 600 seconds.

The invention is also directed to a process for annealing amorphous atorvastatin comprising irradiating amorphous atorvastatin with ultrasound at a frequency ranging from about 15 KHz to about 40 KHz and power of about 100 watts (W) to 4000 watts (W) either in a continuous or pulse for a time period ranging from about 1 second to about 10 hours. In one embodiment, amorphous atorvastatin is irradiated with ultrasound at a frequency of about 15 KHz to about 40 KHz and power of about 100 W to 3000 W in a continuous mode range for a time period of about 10 seconds up to about 10 hours. In another embodiment, amorphous atorvastatin is irradiated from about 1 minute up to about 10 hours with ultrasound at a frequency of about 20-35 KHz and power of about 100 W to 3000 W in a pulse mode range for a pulse time period of about 10 to about 600 seconds.

The Invention is also directed to the annealing processes described above, wherein the amorphous atorvastatin is part of a pharmaceutical composition or formulation prior to the annealing process being applied, each as described herein. For example, amorphous atorvastatin can be admixed with a pharmaceutically acceptable diluent, carrier, or excipient to form, by way of example, a tablet. The tablet can then undergo an annealing process described herein.

As described above, amorphous atorvastatin, either alone or as part of a pharmaceutical composition/formulation, is annealed by temperature, pressure, microwave or ultrasound, each as described herein. Temperature annealing as described herein may be accomplished by any method available to the skilled artisan, for instance, by using an oven. For example, the samples are heated to a certain temperature for set periods of time, each as described herein, and then withdrawn from the oven and allowed to cool to room temperature. Irradiation may be accomplished by, for example, using a microwave oven whereas pressure and ultrasound treatment can be applied using, for example, an ultrasound probe.

According to the invention, an annealing process as described herein can be repeated two or more times.

Also according to the invention, an annealing process as described herein can be performed under an inert atmosphere (i.e., at a reduced oxygen partial pressure) such as nitrogen or under vacuum, in order to minimize degradation during annealing.

According to the invention, amorphous atorvastatin may be exposed to a plasticizer through either gas or liquid phase, either prior to or during an annealing process, each as described herein. With treatment with a plasticizer, an annealing process may be conducted under milder conditions (e.g., lower temperature for thermal/temperature annealing, or lower power for microwave annealing), each as described herein, and thus minimize degradation while still providing the appropriate extent or degree of annealing.

Also according to the invention, amorphous atorvastatin, either alone or as part of a pharmaceutical composition/formulation, may be annealed by two or more annealing processes, each as described herein, simultaneously or consecutively.

Further, the stability of the resulting annealed amorphous atorvastatin can be evaluated. For example, the annealed amorphous atorvastatin can be placed in screw top vials and incubated in a 50° C./20% relative humidity ("RH") chamber and then analyzed according to techniques available to the skilled artisan as described in Example 1.

The Invention is further directed to a composition of matter which is annealed amorphous atorvastatin.

The invention is further directed to annealed amorphous atorvastatin, either alone or as part of a pharmaceutical composition/formulation, prepared by a process as described herein.

The invention is additionally directed to a pharmaceutical composition or formulation comprising annealed amorphous atorvastatin admixed with a pharmaceutically acceptable diluent, carrier, or excipient.

The invention is additionally directed to a pharmaceutical composition or formulation comprising annealed amorphous atorvastatin; at least one pharmaceutically acceptable alkali metal or alkaline earth metal salt (e.g., sodium carbonate, calcium carbonate, calcium hydroxide, magnesium carbonate, magnesium hydroxide, magnesium silicate, magnesium aluminate or aluminum magnesium hydroxide); and a pharmaceutically acceptable diluent, carrier or excipient. Preferably, a pharmaceutical composition or formulation of the invention is an oral pharmaceutical formulation.

As would be understood by one of skill in the art, methods for the preparation of a pharmaceutical composition or formulation suitable for the delivery of annealed amorphous atorvastatin may be found, for example, in *Remington's Pharmaceutical Sciences,* 19th Edition (Mack Publishing Company, 1995), or as provided below for formulations for oral administration. For example, a pharmaceutical composition or formulation containing amorphous atorvastatin can be prepared by any means known in the art including, but not limited to, admixing amorphous atorvastatin with a pharmaceutically acceptable diluent, carrier or excipient and, optionally, at least one pharmaceutically acceptable alkaline earth metal salt, each as described herein.

The annealed amorphous atorvastatin may be administered alone or in combination with one or more other drugs (or as any combination thereof). Generally, the annealed amorphous atorvastatin, whether alone or in combination, will be administered as a formulation in association with one or more pharmaceutically acceptable diluents, carriers or excipients. The terms "diluent", "carrier" and "excipient" may be any diluent, carrier or excipient known in the art including those described in, for example, Remington's Pharmaceutical Sciences, Mack Publishing Co., (A. R. Gennaro edit 1985). As would be understood by one of skill in the art, the choice of diluent, carrier or excipient will to a large extent depend on factors such as the particular mode of administration, the effect of the excipient on solubility and stability, and the nature of the dosage form.

Alternatively, a formulation or composition comprising the annealed amorphous atorvastatin may be stabilized by further comprising at least one pharmaceutically acceptable alkali metal or alkaline earth metal salt such as, but not limited to, those provided in U.S. Pat. Nos. 5,686,104 and 6,126,971, both of which are assigned to the assignee of the Instant application. The alkali metal or alkaline earth metal salt is preferably sodium carbonate, calcium carbonate, calcium hydroxide, magnesium carbonate, magnesium hydroxide, magnesium silicate, magnesium aluminate or aluminum magnesium hydroxide.

Still further, according to the invention, a pharmaceutical formulation of the invention containing amorphous atorvastatin can be annealed at elevated temperature, at elevated pressure, under microwave irradiation, or under ultrasound irradiation, each as described herein.

BRIEF DESCRIPTION OF THE DRAWINGS

FIG. 6b depicts the X-ray powder diffraction patterns of spray-dried amorphous atorvastatin calcium that was annealed for 1 hour at 100° C.

DETAILED DESCRIPTION OF THE INVENTION

Definitions

Figure 1:
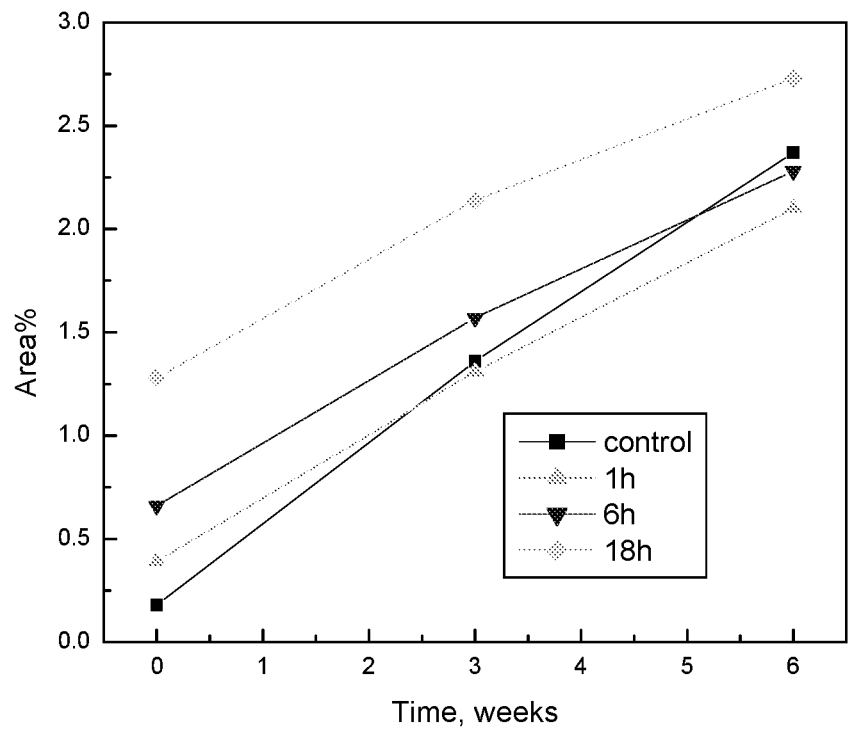
FIG. 1 depicts increases in the level of total degradation products during storage of amorphous atorvastatin calcium at 50° C./20% RH ("RH" refers to relative humidity). The four curves are related to the control and samples that were annealed for 1, 6, and 18 hours at 100° C.

The term "atorvastatin" as used herein refers to [R-(R*, R*)]-2-(4-fluorophenyl)-β,δ-dihydroxy-5-(1-methylethyl)-3-phenyl-4-[(phenylamino)carbonyl]-1H-pyrrole-1-heptanoic add (the free acid form):

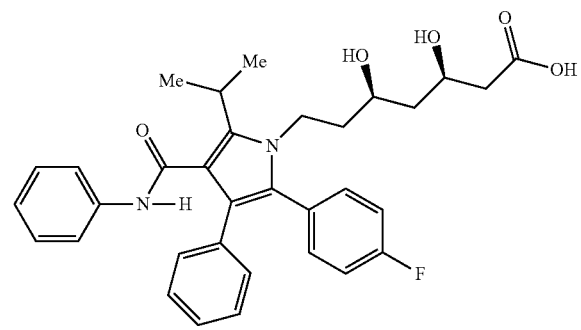 [SMILES: CC(C)c1c(C(=O)Nc2ccccc2)c(-c2ccccc2)c(-c2ccc(F)cc2)n1CC[C@@H](O)C[C@@H](O)CC(=O)O]

and salts, solvates, hydrates and polymorphs thereof. Pharmaceutically acceptable base addition salts of atorvastatin can be formed with metals (e.g., alkali metal or alkaline earth metal salts) or amines (e.g. organic amines). Examples of suitable amines include, but are not limited to, N,N'-dibenzylethylenediamine, chloroprocaine, choline, diethanolamine, dicyclohexylamine, ethylenediamine, N-methylglucamine, and procaine (see, for example, Berge, S. M., et al., "Pharmaceutical Salts", *J. of Pharm. Sci.,* 1977; 66:1).

A preferred form of atorvastatin is atorvastatin calcium; more specifically, atorvastatin hemi-calcium salt trihydrate and marketed under the tradename LIPITOR®.

The term "amorphous atorvastatin" as used herein refers to different types of disordered forms of atorvastatin, as described above, including completely amorphous material, partially amorphous material (e.g., a mixture of crystalline and amorphous), and crystalline mesophases (e.g., liquid-crystal type structures). Amorphous atorvastatin, and the amount of amorphous atorvastatin present, may be characterized by techniques known in the art such as powder x-ray diffraction, solid-state nuclear magnetic resonance (SS-NMR) spectroscopy, or thermal techniques such as differential scanning calorimetry (DSC).

The amorphous atorvastatin used to practice the invention can be prepared by any means known in the art including, but not limited to, those means provided in Lin et al., U.S. Pat. No. 6,087,511, WO 00/71116, WO 01/28999, WO 01/42209, WO 03/078379, or US Published Patent Application 2004/0024046 A1. The amorphous atorvastatin can be prepared by spray-drying or freeze-drying according to the process described in, Published U.S. Patent Application 2005-0032880, and commonly owned, U.S. Provisional Application Ser. No. 60/623,086 field Oct. 28, 2004, or by precipitation from a solution as described in U.S. Provisional Application Ser. No. 60/562,948 filed Apr. 16, 2004, assigned to the same assignee as the instant application. The term "freeze-drying" refers to the process of removing a solvent from a frozen product under reduced pressure. The term "spray-drying" means breaking up liquid mixtures into small droplets and rapidly removing solvent from the mixture.

The annealed amorphous atorvastatin may also exist in unsolvated and solvated forms. The term 'solvate' is used herein to describe a molecular complex comprising annealed amorphous atorvastatin, as described herein, and one or more pharmaceutically acceptable solvent molecules, for example, ethanol. The term 'hydrate' is employed when said solvent is water.

The annealed amorphous atorvastatin can be assessed for its biopharmaceutical properties, such as solubility and solid state and solution stability (across pH), permeability, etc., in order to select the most appropriate dosage form and route of administration for treatment of the proposed indication.

"Annealing" refers to (a) heating the amorphous atorvastatin at a specified temperature, holding the temperature for a set period of time, and then cooling the resulting annealed amorphous atorvastatin; (b) exposing the amorphous atorvastatin to a higher than ambient pressure; (c) irradiating the amorphous atorvastatin with microwave or ultrasound radiation frequency; or (d) a combination thereof. According to the invention, annealing (a), (b), (c) and (d) can be performed in either continuous or pulse mode.

The term "essentially solvent-free system" as used herein refers to a system where no additional solvent is added. The amorphous atorvastatin may contain residual solvent resulting from its synthesis or pharmaceutical processing operations, e.g., wet granulation. For example, amorphous atorvastatin which contains about 2 wt % water or another solvent would be considered "essentially solvent-free".

The term "plasticizer" refers to molecules that increase molecular mobility (e.g., decrease glass transition temperature, or the temperature of the localized motions such as beta-relaxation). Examples of suitable plasticizers include, but are not limited to, alcohols (e.g., methanol, ethanol, glycerol), esters (e.g., ethyl acetate), ketones (e.g., acetone), and other organic and inorganic solvents (e.g., water).

Oral Administration

Annealed amorphous atorvastatin may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Alternatively, a composition or formulation of the invention may be in the form of multiparticulate beads.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from about 1 weight % to about 60 weight % of the dosage form, more typically from about 5 weight % to about 40 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from about 1 weight % to about 25 weight %, preferably from about 3 weight % to about 20 weight % of the dosage form.

Binders are generally used to impart cohesive qualities to a tablet formulation. Typically such tablet formulations contain about 0-10 weight % binder. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise stabilizing alkali metal or alkaline earth metal salts. The alkali metal or alkaline earth metal salt is preferably sodium carbonate, calcium carbonate, calcium hydroxide, magnesium carbonate, magnesium hydroxide, magnesium silicate, magnesium aluminate or aluminum magnesium hydroxide. Typically, such tablet formulations contain about 10-30 weight % stabilizing alkaline earth metal salts.

Tablets may also optionally comprise surface active agents, such as sodium lauryl sulfate and polysorbate 80, and glidants such as silicon dioxide and talc. When present, surface active agents may comprise from about 02 weight % to about 5 weight % of the tablet, and glidants may comprise from about 02 weight % to about 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from about 0.25 weight % to about 10 weight %, preferably from about 0.5 weight % to about 3 weight % of the tablet.

Other possible ingredients include anti-oxidants, colourants, flavouring agents, preservatives and taste-masking agents.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human use are typically pliable water-soluble or water-swellable thin film dosage forms which may be rapidly dissolving or mucoadhesive and typically comprise annealed amorphous atorvastatin, a film-forming polymer, a binder, a solvent, a humectant, a plasticiser, a stabiliser or emulsifier, a viscosity-modifying agent and a solvent. Some components of the formulation may perform more than one function.

The film-forming polymer may be selected from natural polysaccharides, proteins, or synthetic hydrocolloids and is typically present in the range of about 0.01 to about 99 weight %, more typically in the range of about 30 to about 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14, by Verma at al (2001). The use of chewing gum to achieve controlled release is described in WO 00/35298.

The following non-limiting examples illustrate the invention.

EXAMPLE 1

General Method for Stabilizing Amorphous Atorvastatin by Annealing at Elevated Temperature(Continuous Mode)

Amorphous atorvastatin calcium was prepared by spray-drying according to the procedure described in U.S. patent applications, commonly owned, Published US Patent Application 2005-0032880, Ser. No. 60/623,086. The vials used in the example were commercially available source from Wheaton, Milville, N.J.

The amorphous atorvastatin calcium was loaded into 20 ml glass vials (approximately 1 g per vial), and heated at 100±5° C. for 1, 6, and 18 hours in an oven. After heating, the powder was transferred from the vials to 15 ml amber screw-cap bottles, and set-up on stability at 50° C./20% RH. In addition, unannealed amorphous atorvastatin calcium, which was loaded in 15 ml amber screw-cap bottles, was placed on stability as a control.

Analysis

High Pressure Liquid Chromatography (HPLC)

The annealed amorphous atorvastatin calcium was analyzed for impurities and atorvastatin degradation products using HPLC, by evaluating the ratio of peak integration compared to the total integrated peak areas. Thus, 27 mg of either control or annealed amorphous atorvastatin calcium was wetted with 5 mL of tetrahydrofuran, followed by addition of a solution of 1:1 tetrahydrofuran: acetonitrile (v:v) to a total volume of 50 mL. The material was analyzed by HPLC (Zorbax SB C8 column, 25.0 cm×4.6 mm, HPLC: Hewlett Packard 1100 series, 20 µl injection volume, flow of 1.5 mL/min). The elution used a linear gradient starting from 67:21:12 (v:v:v) and switching to 54:34:12 (v:v:v) of 0.05M ammonium acetate buffer (pH 5.0):acetonitrile:tetrahydrofuran after 40 minutes (100% of the latter mixture after 55 minutes).

Solid State Nuclear Magnetic Resonance (SSNMR) Spectroscopy

Approximately 80 mg of sample was tightly packed into a 4 mm ZrO spinner for each sample analyzed. All spectra were collected at 293 K and ambient pressure on a Bruker-Biospin 4 mm BL HFX CPMAS probe positioned into a wide-bore Bruker-Biospin Avance DSX 500 MHz NMR spectrometer. The samples were oriented at the magic angle and spun at 15.0 kHz, corresponding to the maximum specified spinning speed for the 4 mm spinners. The fast spinning speed minimized the intensities of the spinning side bands. $^{19}F$ solid-state spectra were collected using proton decoupled magic angle spinning (MAS) experiment. The proton-decoupling field of approximately 65 kHz was applied. The probe background was reduced by subtracting signal from interleaved scans, during which a $^{19}F$ presaturation pulse was applied. Typically, 32 scans were collected on each $^{19}F$ MAS spectrum. The recycle delay was set to 15 seconds to ensure acquisition of quantitative spectra. The spectra were referenced using an external sample of trifluoroacetic acid (diluted to 50% by volume with $H_2O$), setting its resonance to −76.54 ppm.

Powder X Ray Diffraction (PXRD)

The X-ray powder diffraction pattern of amorphous atorvastatin calcium and annealed amorphous atorvastatin calcium was determined using a Bruker D5000 diffractometer (Madison, Wis.) equipped with copper radiation (Cu $K_\alpha$). Data were collected from 3.0 to 40.0 degrees in two theta using a step size of 0.04 degrees and a step time of 1.0 seconds. The divergence and scattering slits were set at 1 mm, and the receiving slit was set at 0.6 mm. Diffracted radiation was detected by a Kevex PSI detector. An alumina standard was analyzed to check the instrument alignment. Data were collected and analyzed using Bruker AXS software Version 7.0. Samples were prepared for analysis by placing them in a quartz holder. The sample is typically placed into a quartz holder which has a cavity.

Results

Figure 2:
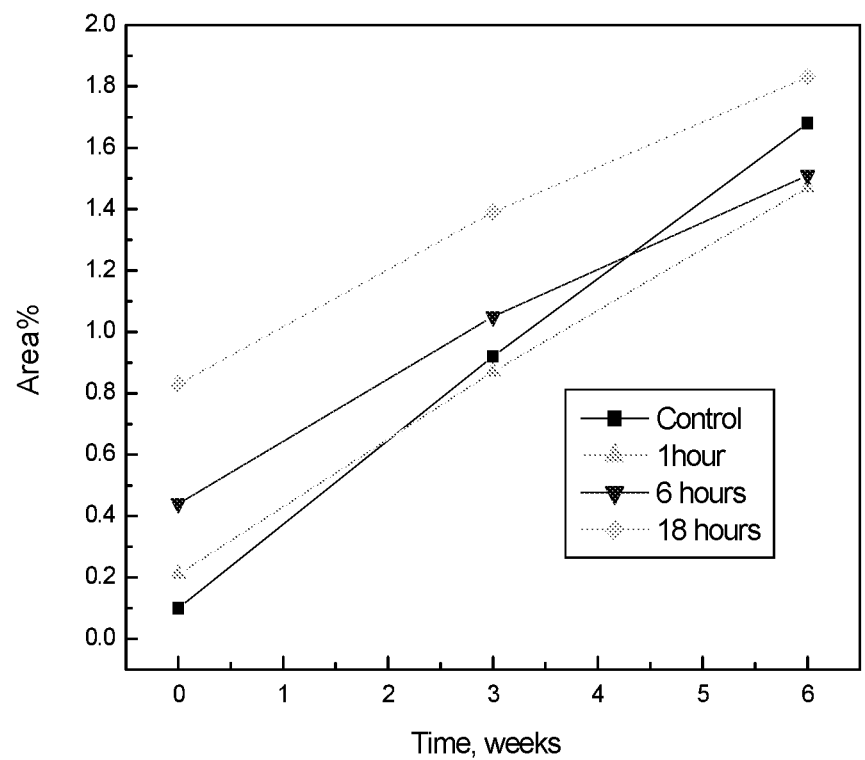
FIG. 2 depicts level of total oxidative degradation products as a function of time during storage of amorphous atorvastatin calcium at 50% C/20% relative humidity. The four curves are related to the control and samples that were annealed for 1, 6, and 18 hours at 100° C.
Figure 3:
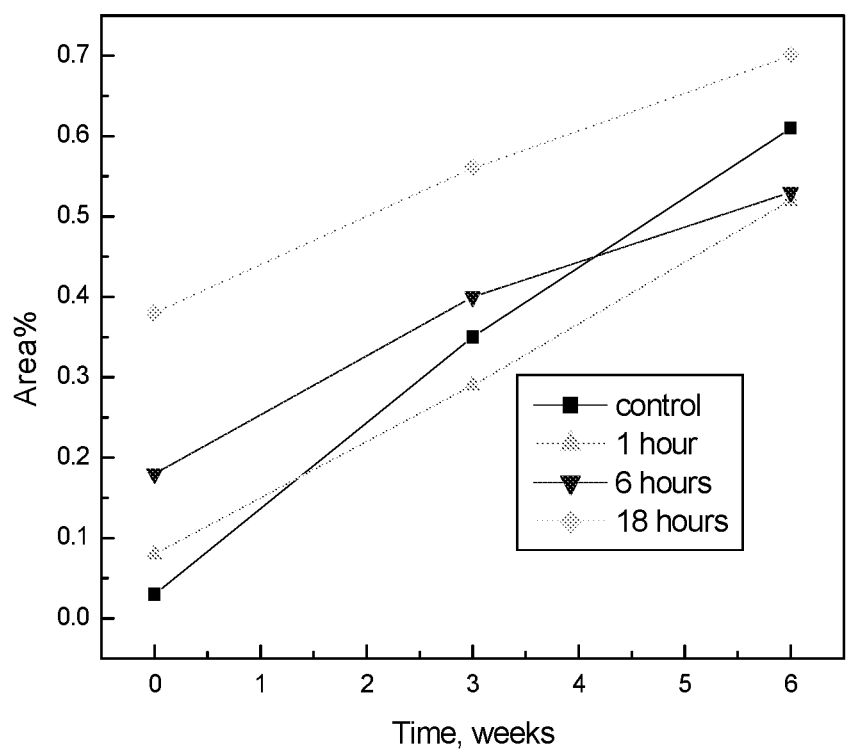
FIG. 3 depicts level of degradation product 1 (Scheme 1) as a function of time during storage of amorphous atorvastatin calcium at 50° C./20% relative humidity. The four curves are related to the control and samples that were annealed for 1, 6, and 18 hours at 100° C.
Figure 4:
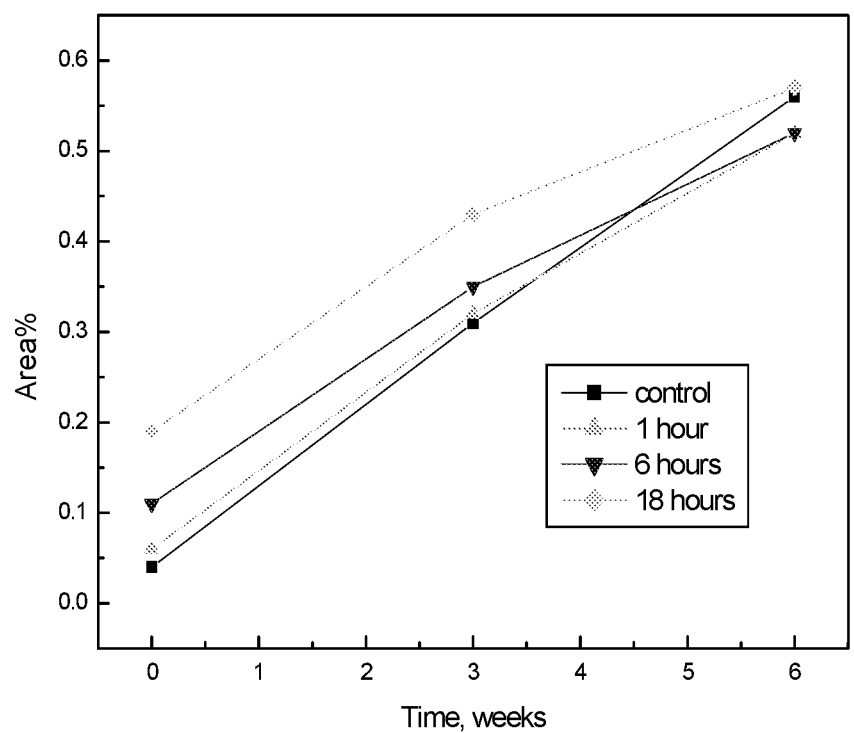
FIG. 4 depicts level of degradation product 2 (Scheme 2) as a function of time during storage of amorphous atorvastatin calcium at 50° C./20% relative humidity. The four curves are related to the control and samples that were annealed for 1, 6, and 18 hours at 100° C.

Stability data obtained for three annealed samples and the control sample are graphically illustrated in FIGS. 1 to 4. It can be seen that the annealing resulted in some degradation as expressed in higher level of two individual degradants (FIGS. 3, 4), total oxidation products (FIG. 2), and total degradation products (FIG. 1) at t=0 (first time point on FIGS. 1 to 4). However, after storage for 6 weeks at 50° C./20% RH, the level of degradants was lower in samples annealed for 1 and 6 hours comparing with the control sample. In order to express stabilization by annealing in a more quantitative term, relative degradation rate constants, $k_{rel}$, were determined from the data presented in FIGS. 1 to 4. The $k_{rel}$ were calculated using Eq. 1:

$$k_{rel}=(k/k0)*100\%$$ Eq. 1 where k is the zero order rate constant for annealed samples, and k0 is the zero order rate constant for the control sample; k and k0 were determined from the data presented in FIGS. 1 to 4.

The relative rate constants ($k_{rel}$) are given in Table 1. Relative rates below 100% mean that the degradation rate is slower for annealed samples and can be used as a quantitative expression of the stabilization by annealing whereas numbers greater than 100 percent would indicate destabilization. For example, the relative degradation rate for total degradation products for the sample that was annealed for 18 hours was 66 percent (bolded and Italicized in Table 1); I.e., 34 percent less than in the control.

TABLE 1

Relative degradation rate constants ($k_{rel}$) of amorphous atorvastatin calcium relative to control after annealing at different conditions*

| Annealing time at 100° C., hours | Relative rate constant, (k/k0) * 100% | | | |
|---|---|---|---|---|
| | total degradants | total oxidative degradants | degradant 1, rrt 1.67 | degradant 2, rrt 2.16 |
| 0 hours (control) | 100 | 100 | 100 | 100 |
| 1 hour | 78 | 80 | 76 | 88 |
| 6 hours | 74 | 68 | 60 | 79 |
| 18 hours | 66 | 63 | 55 | 73 |

*$k_{rel}$ = (k/k0) * 100%. k is the zero order rate constant, and k0 is the zero order rate constant for the control sample. k and k0 were determined from data represented in FIGS. 1 to 4. "rrt" means relative retention time Overall, the lower level of degradants at the 6-week time point for samples annealed for 1 and 6 hours (FIGS. 1 to 4), and lower rates of degradation in the annealed materials (Table 1) demonstrate that annealing increased the thermal stability of atorvastatin calcium.

Figure 5:
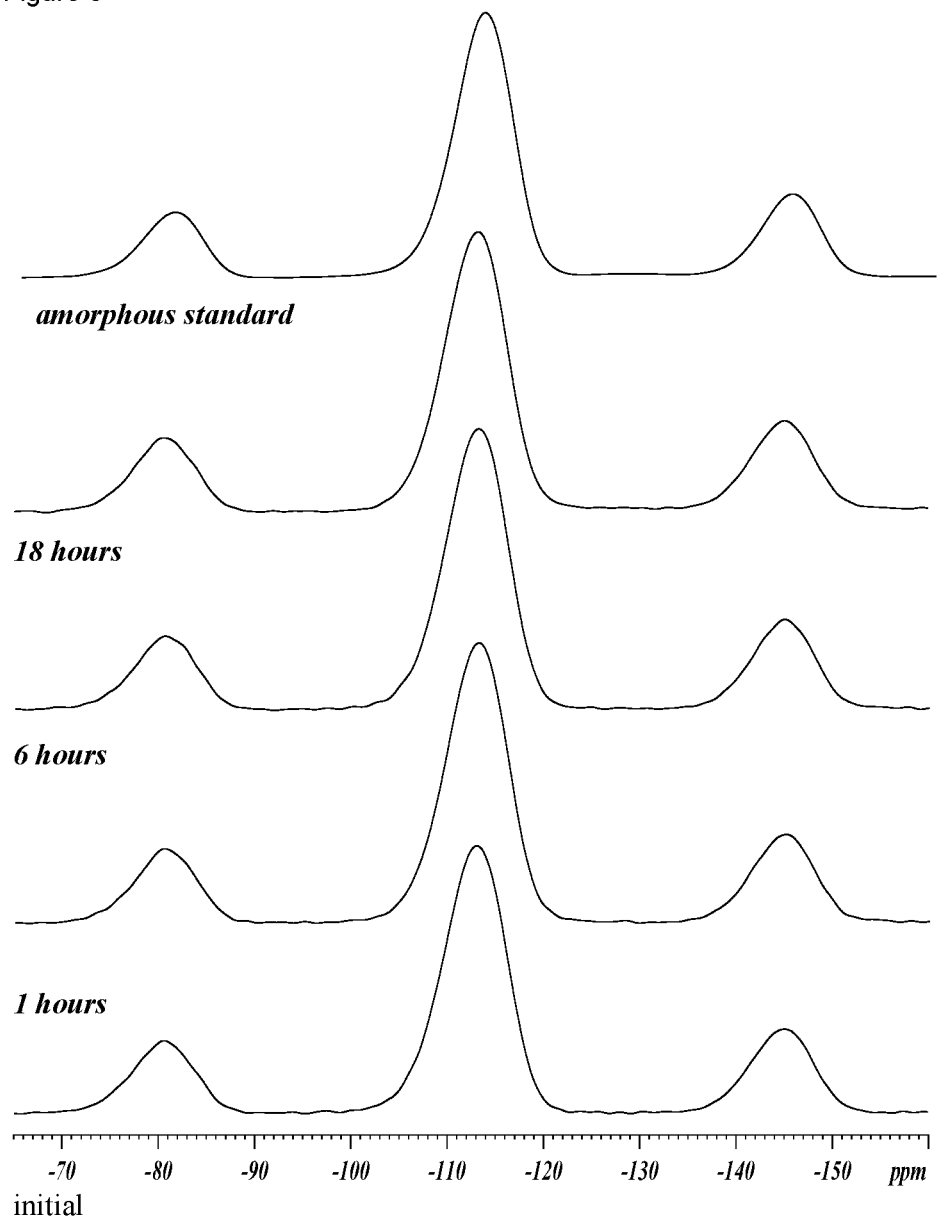
FIG. 5 depicts a solid-state $^{19}$F nuclear magnetic resonance (NMR) spectrum of atorvastatin calcium samples from Example 1. A standard spectrum is also shown for comparison.
Figure 6A:
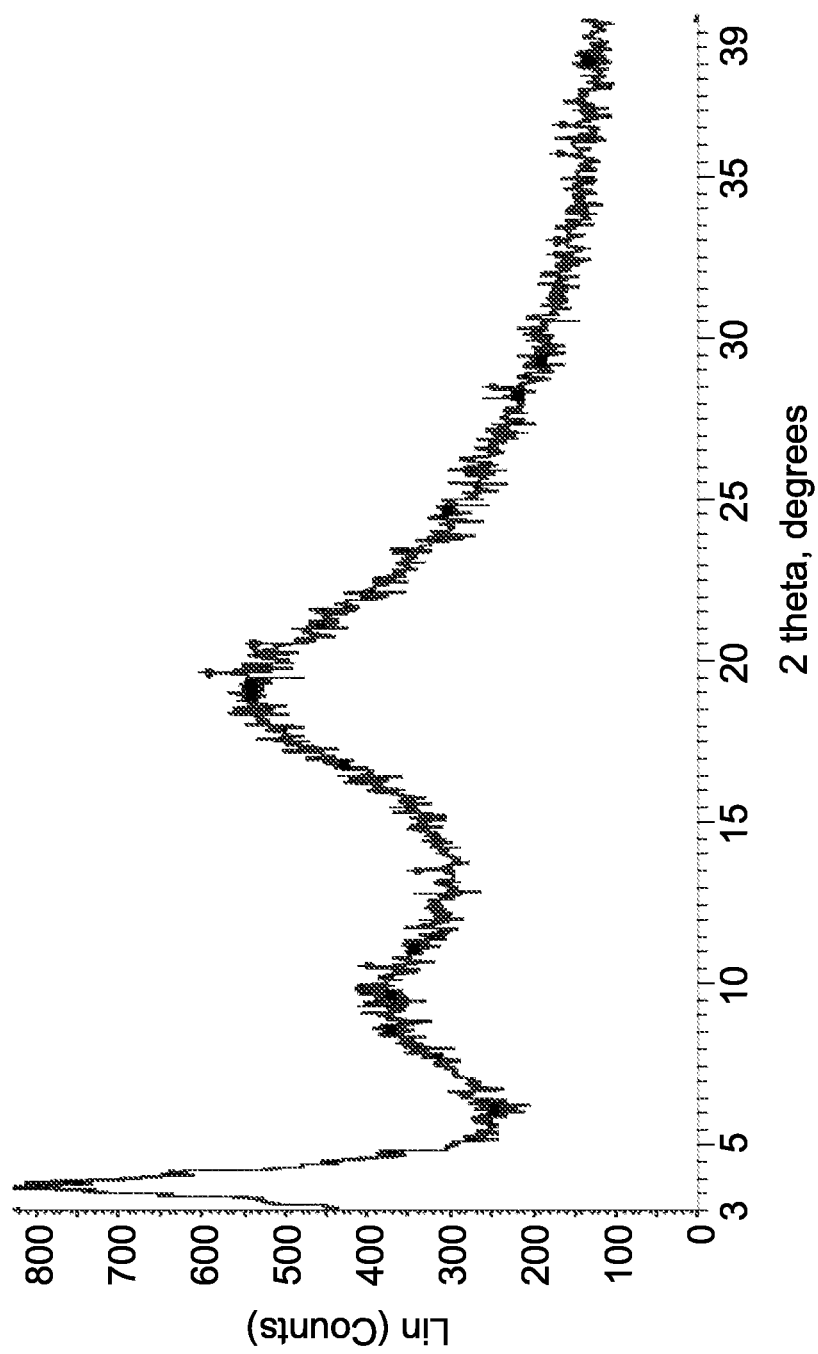
FIG. 6a depicts the X-ray powder diffraction patterns of spray-dried unannealed (control sample) amorphous atorvastatin calcium.
Figure 6C:
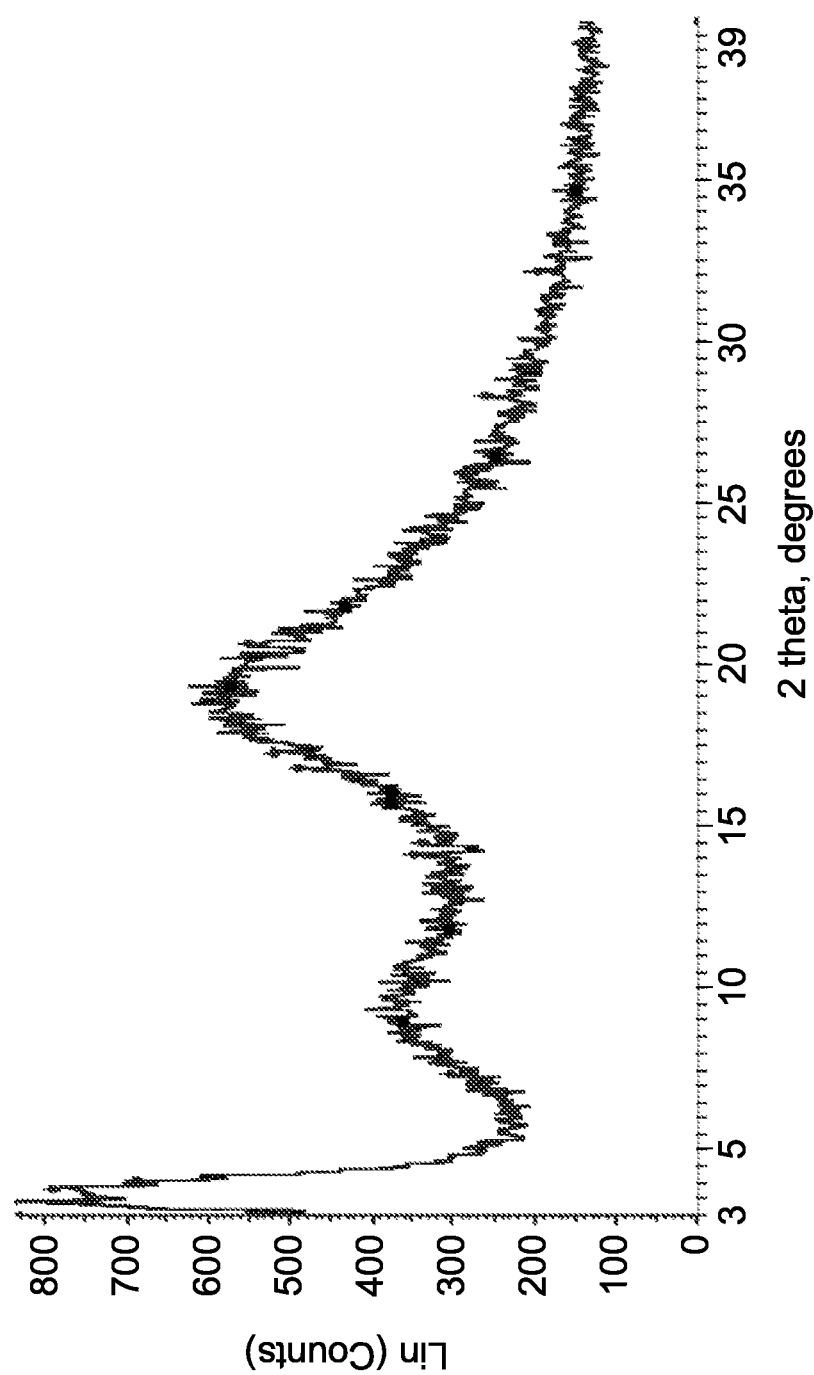
FIG. 6c depicts the X-ray powder diffraction patterns of spray-dried amorphous atorvastatin calcium that was annealed for 6 hours at 100° C.
Figure 6D:
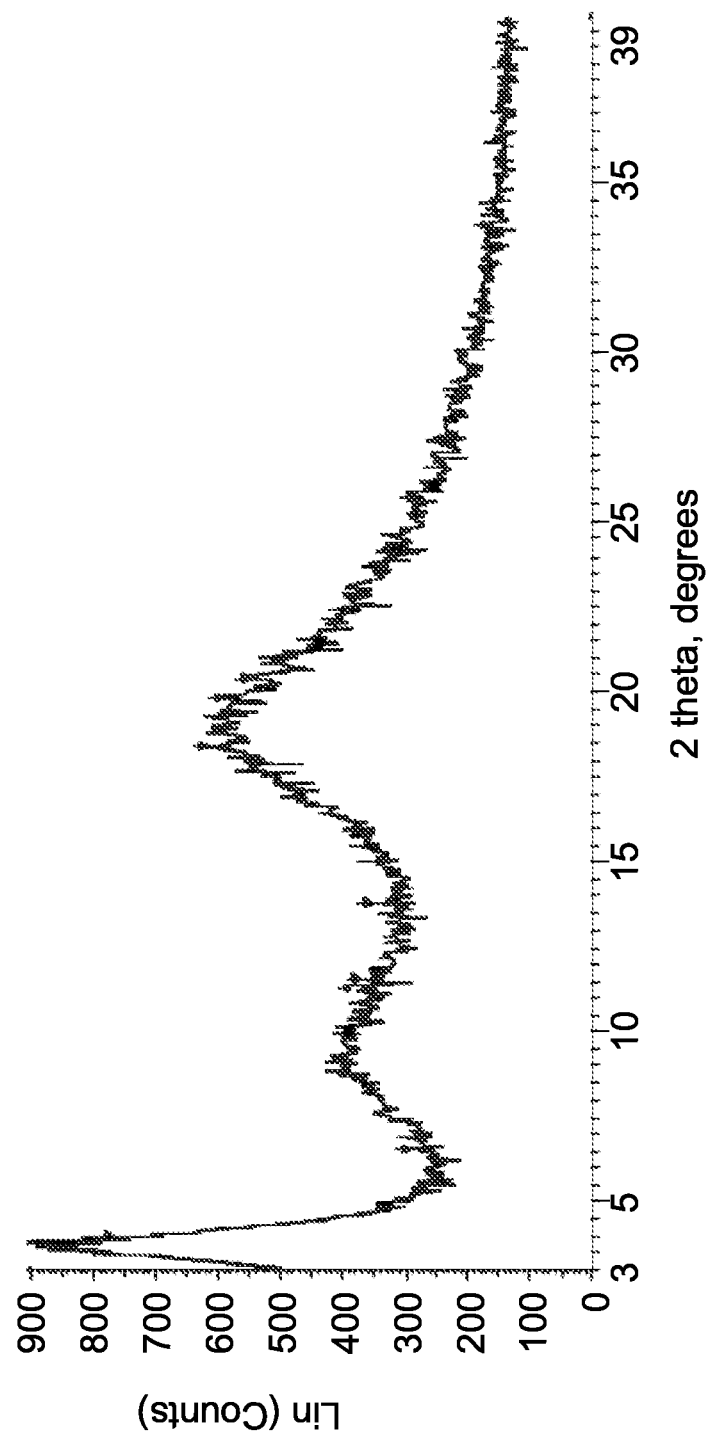
FIG. 6d depicts the X-ray powder diffraction patterns of spray-dried amorphous atorvastatin calcium that was annealed for 18 hours at 100° C.

FIGS. 5 and 6a-6d indicate that the SSNMR and PXRD spectra of annealed amorphous atorvastatin samples were similar to a control sample of unannealed amorphous atorvastatin calcium.

Summary of Example 1

Annealed amorphous atorvastatin is surprisingly more stable than non-annealed amorphous atorvastatin. This is an example of amorphous atorvastatin calcium which is stabilized by annealing at elevated temperature (i.e. temperature annealing). As indicated in the stability data included in Example 1, annealed amorphous atorvastatin calcium degraded to some extent during annealing as expressed in higher levels of two individual degradants (FIGS. 3, 4), as well as total oxidation products (FIG. 2) and total degradation products (FIG. 1) at t=0 (first time point on FIGS. 1 to 4). The structure of the two degradants are depicted in Schemes 1 and 2. However, after storage for 6 weeks at 50° C./20% RH, the level of degradants was lower in samples annealed for 1 and 6 hours compared with the control sample.

Scheme 1

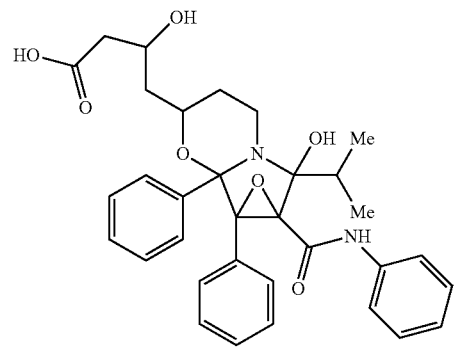

Degradant 1, HPLC relative retention time 1.67

Scheme 2

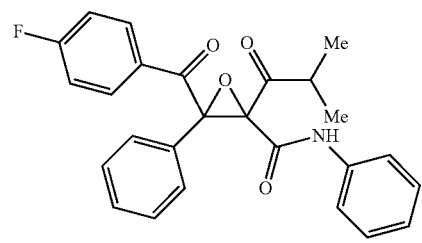

Degradant 2, HPLC relative retention time 2.16

The stability of annealed amorphous atorvastatin calcium compared to non-annealed amorphous atorvastatin calcium can be expressed in terms of relative degradation rate constants as summarized in Table 1 in Example 1. Relative rates below 100% mean that the degradation rate is slower for annealed samples and can be used as a quantitative expression of the stabilization by annealing whereas numbers equaling or greater than 100 percent indicate destabilization. For example, the relative degradation rate for total degradation products for the sample that was annealed for 18 hours was 66 percent (bolded and Italicized in Table 1 infra Example 1); i.e., 34 percent less than in the control.

The results summarized in Table 1 demonstrate that annealed amorphous atorvastatin calcium can be stored for longer periods than non-annealed amorphous atorvastatin calcium. Moreover, annealed amorphous atorvastatin calcium can be used to prepare pharmaceutical dosage forms with enhanced stability profiles as compared to dosage forms containing non-annealed amorphous atorvastatin calcium.

EXAMPLE 2

General Method for Stabilizing Amorphous Atorvastatin by Annealing at Greater than Atmospheric Pressure(Continuous Mode)

Spray-dried or freeze-dried amorphous atorvastatin calcium is pressurized to about 1 kBar at about 50° C. for about 30 min, about 1 hour, and about 6 hours.

EXAMPLE 3

General Method for Stabilizing Amorphous Atorvastatin by Microwave Irradiation(Continuous Mode)

Spray-dried or freeze-dried amorphous atorvastatin calcium is irradiated with microwave frequency of about 2.45

GHz, power of about 20 W to 120 W in a continuous mode range in time period of about 10 seconds up to about 10 hours using Microwave Power Generator Model 520A (Resonance Instrument Inc., 9054 Terminal Ave., Skokie, Ill. 60077). A circular reaction cavity is fabricated to meet the requirements of testing pharmaceutical samples.

EXAMPLE 4

General Method for Stabilizing Amorphous Atorvastatin by Microwave Irradiation(Pulse Mode)

Spray-dried or freeze-dried amorphous atorvastatin calcium is irradiated from about 1 minute up to about 10 hours with microwave frequency of about 2.45 GHz, power of about 20 W to 120 W in a pulse mode range for a pulse time period of about 10 to about 600 seconds using Microwave Power Generator Model 520A (Resonance Instrument Inc., 9054 Terminal Ave., Skokie, Ill. 60077). A circular reaction cavity is fabricated to meet the requirements of testing pharmaceutical samples.

EXAMPLE 5

General Method for Stabilizing Amorphous Atorvastatin by Ultrasonic Irradiation(Continuous Mode)

Spray-dried or freeze-dried amorphous atorvastatin calcium is irradiated with ultrasonic frequency of about 20 to 35 KHz, power of about 100 W to 3000 W in a continuous mode range in time period of about 10 seconds up to about 10 hours, using The Ultrasonic Generator (Active Ultrasonics Sarl, Pults-Godet 6A, CH-2000 Neuchatel, Switzerland). The instrument has 3 separate probes that generate the following frequencies of ultrasound: 20 kHz, 30 kHz and 35 kHz. Specially designed cup-horns are fabricated to meet the requirements of testing pharmaceutical samples.

EXAMPLE 6

General Method for Stabilizing Amorphous Atorvastatin by Ultrasonic Irradiation(Pulse Mode)

Spray-dried or freeze-dried amorphous atorvastatin calcium is irradiated from 1 minute up to 10 hours with ultrasonic frequency of 20 to 35 KHz, power 100 to 3000 watts in a pulse mode range for a pulse time period of 10 to 600 seconds using The Ultrasonic Generator (Active Ultrasonics Sarl, Puits-Godet 6A, CH-2000 Neuchatel, Switzerland). The instrument has 3 separate probes that generate the following frequencies of ultrasound: 20 kHz, 30 kHz and 35 kHz. Specially designed cup-horns are fabricated to meet the requirements of testing pharmaceutical samples.

EXAMPLE 7

General Method for Stabilizing Pharmaceutical Formulation Containing Amorphous Atorvastatin Ca by Ultrasonic Irradiation(Pulse Mode)

A pharmaceutical formulation containing amorphous atorvastatin calcium is irradiated from 1 minute up to 10 hours with ultrasonic frequency of 20 to 35 KHz, power 100 to 3000 watts in a pulse mode range for a pulse time period of 10 to 600 seconds using The Ultrasonic Generator (Active Ultrasonics Sarl, Puits-Godet 6A, CH-2000 Neuchatel, Switzerland). The instrument has 3 separate probes that generate the following frequencies of ultrasound: 20 kHz, 30 kHz and 35 kHz. Specially designed cup-horns are fabricated to meet the requirements of testing pharmaceutical samples.

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. Accordingly, the invention is limited only by the following claims.

What is claimed is:

1. A process for annealing amorphous atorvastatin comprising irradiating amorphous atorvastatin with microwave at a frequency ranging from about 1 GHz to about 100 GHz and power of about 1 watt to about 3000 watts either in a continuous or pulse mode for a time period ranging from about 1 second to about 10 hours.

2. The process of claim 1, wherein said amorphous atorvastatin is irradiated with microwave at a frequency of about 2.45 GHz and power about 10 W to about 500 W in a continuous mode range for a time period of about 10 seconds up to about 10 hours.

3. The process of claim 1, wherein said amorphous atorvastatin is irradiated from about 1 minute up to about 10 hours with microwave at a frequency of about 2.45 GHz and power about 1 W to about 3000 W in a pulse mode range for a time period of about 10 to about 600 seconds.

4. The process of claim 1, wherein said amorphous atorvastatin is amorphous atorvastatin calcium.

5. The process of claim 1, wherein said amorphous atorvastatin is admixed with a pharmaceutically acceptable diluent, carrier, or excipient prior to said irradiating step.

6. A process for annealing amorphous atorvastatin comprising irradiating amorphous atorvastatin with ultrasound at a frequency ranging from about 15 KHz to about 40 KHz and power of about 100 watts to 4000 watts either in a continuous or pulse mode range for a time period ranging from about 1 second to about 10 hours.

7. The process of claim 6, wherein said amorphous atorvastatin is irradiated with ultrasound at a frequency of about 15 KHz to about 40 KHz and power of about 100 W to 3000 W in a continuous mode range for a time period of about 10 seconds up to about 10 hours.

8. The process of claim 6, wherein said amorphous atorvastatin is irradiated from about 1 minute up to about 10 hours with ultrasound at a frequency of about 20-35 KHz and power of about 100 W to 3000 W in a pulse mode range for a time period of about 10 to about 600 seconds.

9. The process of claim 6, wherein said amorphous atorvastatin is amorphous atorvastatin calcium.

10. The process of claim 6, wherein said amorphous atorvastatin is admixed with a pharmaceutically acceptable diluent, carrier, or excipient prior to said irradiating step.

11. The process of claim 1, or 6, wherein said amorphous atorvastatin is treated with a plasticizer prior to or during the annealing process.

* * * * *